(12) United States Patent
Goede et al.

(10) Patent No.: US 8,375,940 B2
(45) Date of Patent: *Feb. 19, 2013

(54) STORAGE SYSTEM FOR POWDERED PHARMACEUTICALS AND INHALER EQUIPPED WITH THIS SYSTEM

(75) Inventors: Joachim Goede, Hanau (DE); Karl-Heinz Lange, Bunde (DE)

(73) Assignee: Almirall, S.A., Barcelona (ES)

( * ) Notice: Subject to any disclaimer, the term of this patent is extended or adjusted under 35 U.S.C. 154(b) by 343 days.

This patent is subject to a terminal disclaimer.

(21) Appl. No.: 11/753,681

(22) Filed: May 25, 2007

(65) Prior Publication Data
US 2007/0215152 A1 Sep. 20, 2007

Related U.S. Application Data

(62) Division of application No. 09/739,170, filed on Dec. 18, 2000, now Pat. No. 7,234,464.

(30) Foreign Application Priority Data

Dec. 18, 1999 (DE) .................................. 199 61 300

(51) Int. Cl.
*A61M 15/00* (2006.01)
(52) U.S. Cl. .......... 128/203.15; 128/200.14; 128/200.23
(58) Field of Classification Search ............. 128/203.12, 128/203.15, 203.18, 203.22
See application file for complete search history.

(56) References Cited

U.S. PATENT DOCUMENTS

| 2,587,215 A | 2/1952 | Priestly |
| 3,815,754 A | 6/1974 | Rosenberg |
| 5,002,048 A | 3/1991 | Makeij |
| 5,007,419 A | 4/1991 | Weinstein et al. |
| 5,048,514 A | 9/1991 | Ramella |
| 5,161,524 A | 11/1992 | Evans |
| 5,169,029 A | 12/1992 | Behar et al. |
| 5,207,217 A | 5/1993 | Cocozza et al. |
| 5,301,666 A | 4/1994 | Lerk et al. |
| 5,394,868 A | 3/1995 | Ambrosio et al. |
| 5,441,060 A | 8/1995 | Rose et al. |
| 5,522,380 A | 6/1996 | Dwork |
| 5,524,613 A | 6/1996 | Haber et al. |
| 5,544,647 A | 8/1996 | Jewett et al. |
| 5,603,401 A | 2/1997 | Brunner |
| 5,664,557 A | 9/1997 | Makeij |

(Continued)

FOREIGN PATENT DOCUMENTS

| CA | 2316345 C | 7/1999 |
| DE | 4436854 | 4/1996 |

(Continued)

OTHER PUBLICATIONS

Chinese Office Action and cited prior art references mailed Nov. 28, 2003.

(Continued)

*Primary Examiner* — Darwin Erezo
(74) *Attorney, Agent, or Firm* — Faegre Baker Daniels

(57) ABSTRACT

In order to improve the administration of powdered pharmaceuticals, the invention proposes a storage system for powdered pharmaceuticals, in particular for use or integration in a powder inhaler, for receiving a multiplicity of doses of at least one medically active substance, with at least two storage spaces (4) which are separate from each other and are each intended to hold a multiplicity of doses of a medically active substance, and the invention also proposes an inhaler for powdered pharmaceuticals, the inhaler comprising such a pharmaceutical powder cartridge system (1) as an integral part or as an exchangeable part.

10 Claims, 4 Drawing Sheets

U.S. PATENT DOCUMENTS

| | | | |
|---|---|---|---|
| 5,687,710 A | 11/1997 | Ambrosio et al. | |
| 5,702,362 A | 12/1997 | Herold et al. | |
| 5,769,073 A | 6/1998 | Eason et al. | |
| 5,778,873 A | 7/1998 | Braithwaite | |
| 5,829,434 A | 11/1998 | Ambrosio et al. | |
| 5,840,279 A | 11/1998 | Narodylo et al. | |
| 5,857,457 A | 1/1999 | Hyppola | |
| 5,911,937 A | 6/1999 | Hekal | |
| 5,924,417 A | 7/1999 | Braithwaite | |
| 5,947,274 A | 9/1999 | Taskis et al. | |
| 5,964,417 A | 10/1999 | Amann | |
| 6,014,972 A | 1/2000 | Sladek | |
| 6,054,082 A | 4/2000 | Heide | |
| 6,065,471 A | 5/2000 | Schaeffer et al. | |
| 6,071,498 A | 6/2000 | Narodylo et al. | |
| 6,321,747 B1 | 11/2001 | Dmitrovic et al. | |
| 6,332,461 B1 | 12/2001 | Hyppola | |
| 6,443,152 B1 | 9/2002 | Lockhart et al. | |
| 6,488,648 B1 | 12/2002 | Matsugi et al. | |
| 7,234,464 B2 * | 6/2007 | Goede et al. | 128/203.15 |
| 2001/0027789 A1 | 10/2001 | Goede | |

FOREIGN PATENT DOCUMENTS

| | | |
|---|---|---|
| DE | 19522415 A1 | 1/1997 |
| DE | 19647947 | 5/1998 |
| DE | 19757208 | 6/1999 |
| JP | 9301400 A | 11/1997 |
| MX | PA02005279 A | 9/2003 |
| WO | WO9203175 | 3/1992 |
| WO | WO95/31237 A1 | 11/1995 |
| WO | WO0064519 | 11/2000 |
| WO | WO01/39823 A1 | 6/2001 |
| WO | WO01/41849 A1 | 6/2001 |
| WO | WO01/43800 A1 | 6/2001 |

OTHER PUBLICATIONS

European Search Report mailed May 22, 2001.
German Search Report dated Jul. 4, 2000.

* cited by examiner

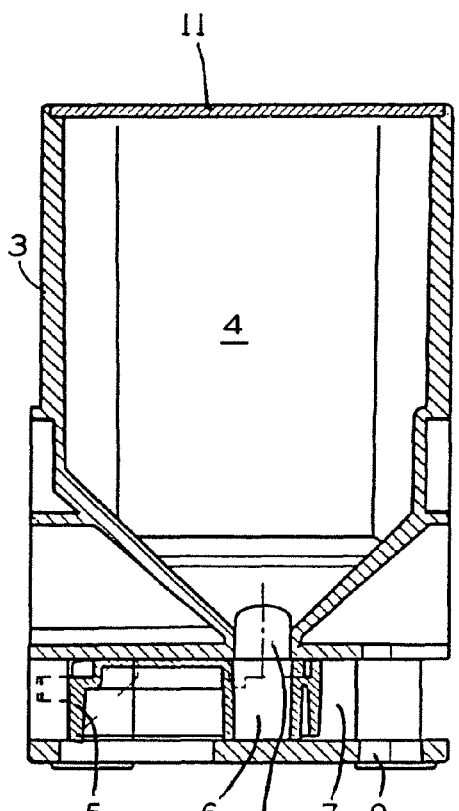
FIG_4
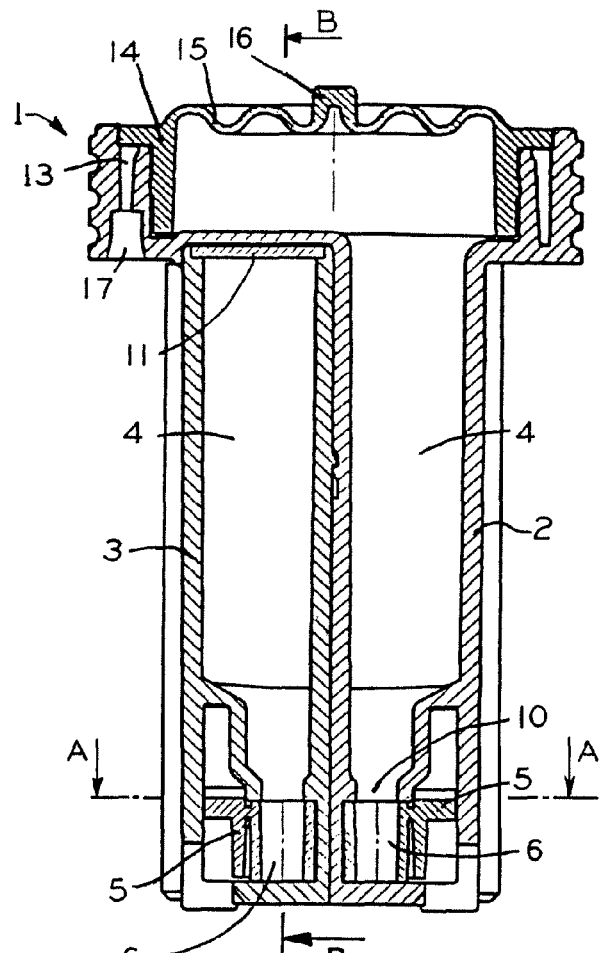
FIG_2
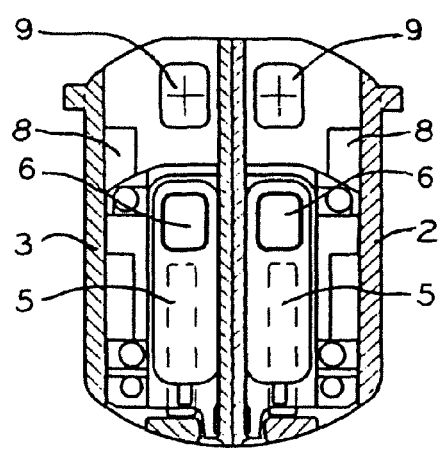
FIG_3

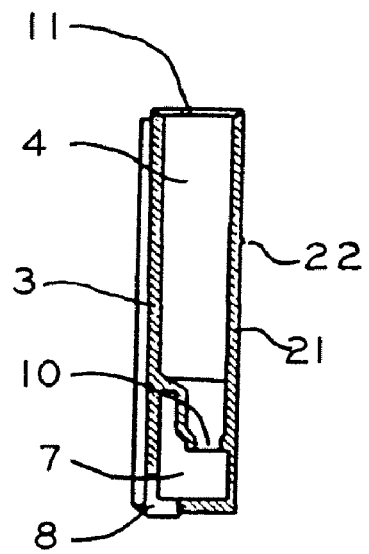
FIG_5
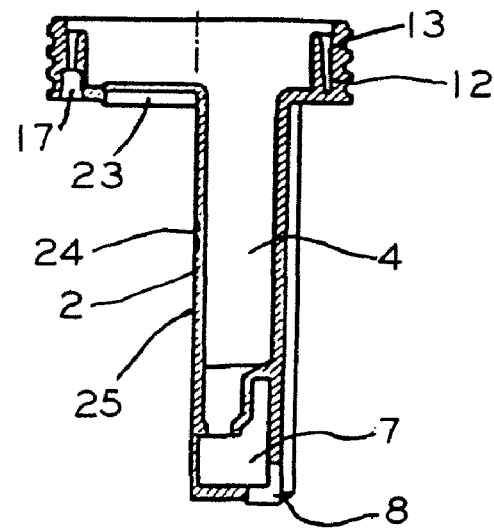
FIG_6
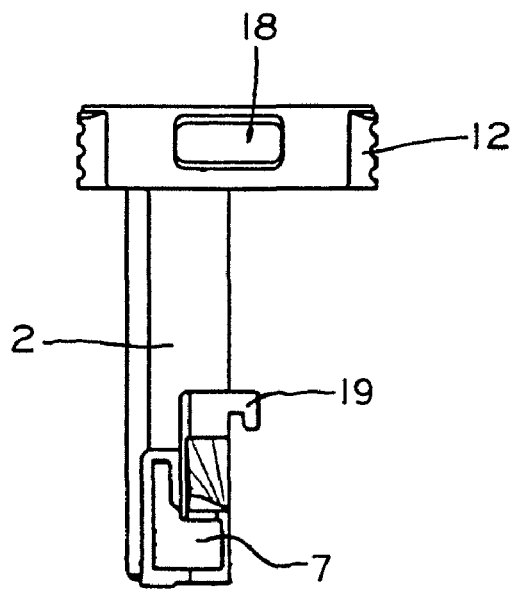
FIG_7

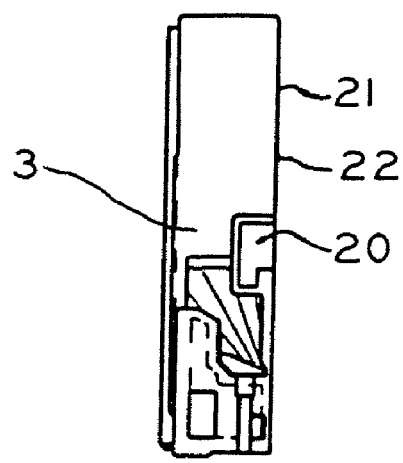
FIG_8
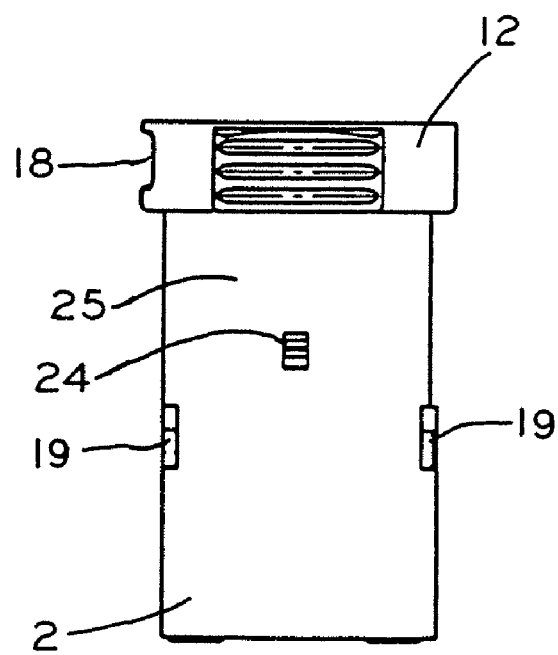
FIG_9

STORAGE SYSTEM FOR POWDERED PHARMACEUTICALS AND INHALER EQUIPPED WITH THIS SYSTEM

CROSS-REFERENCE TO RELATED APPLICATIONS

This is a Divisional of U.S. patent application Ser. No. 09/739,170 filed Dec. 18, 2000, now U.S. Pat. No. 7,234,464, the disclosure of which is hereby expressly incorporated by reference herein.

The invention relates to a storage system for powdered pharmaceuticals, in the form of a pharmaceutical powder cartridge system, and to an inhaler equipped with this system.

BACKGROUND OF THE INVENTION

In the field of treatment of bronchial diseases, and also of other diseases in which medication can be given via the airways, it is known not only to atomize solutions or suspensions into inhalable aerosols but also to administer powdered medicaments. Many examples of such medicaments are described in the literature, and of these we refer purely by way of illustration to WO 93/11773, EP 0 416 950 A1 and EP 0 416 951 A1.

A customary form of administration in this connection is delivery via an inhalation device (inhaler).

Known inhalers for powdered pharmaceuticals include those for administration of a single dose and also inhalation devices which have a reservoir for a plurality of pharmaceutical doses. In this connection, it is known either to provide separate storage spaces for each individual dose or to provide one single receiving space for receiving a multiplicity of doses of a medicament.

Known inhalers in which a multiplicity of individual doses are provided in separate storage spaces include those in which individual areas of the inhaler are each filled with a pharmaceutical dose.

An example of such an inhaler is described in U.S. Pat. No. 5,301,666. However, it is also known to accommodate a multiplicity of pharmaceutical powder doses in separate areas, so-called blister packs. An example of such a blister pack for use with an inhaler is described in DE 44 00 083 C2. Such a blister pack, which is designed at the same time as a disposable inhaler, is described for example in DE 44 00 084 A1.

An inhalation device into which blister packs can be inserted, which each have separate storage spaces for individual doses of a powdered pharmaceutical and which can be emptied one after another with the aid of the inhalation device, is described, for example, in DE 195 23 516 C1.

Many examples of inhalers with a storage space for a multiplicity of pharmaceutical doses are described in the prior art. One example with an exchangeable storage container is described in German Patent Specification 846 770, and another in WO 95/31237.

An important problem with inhalation systems in which a multiplicity of doses of a medically active substance are accommodated in a common storage space concerns the apportioning of an individual dose for one individual inhalation. In this connection, a great many solutions have been proposed, for example those which are described in U.S. Pat. No. 2,587,215 and U.S. Pat. No. 4,274,403. Other types of arrangements for metering an individual dose of pharmaceutical powder from a storage space for a multiplicity of pharmaceutical doses are described in WO 92/09322, WO 93/16748 and DE 35 35 561 C2 and in GB 2 165 159 A. An exchangeable cartridge for receiving a multiplicity of doses of a pharmaceutical powder with an integrated metering slide is known from DE 195 22 415 A1.

Another important problem with inhalation of pharmaceutical powders concerns the breakdown of the galenic powder formulations into particles which can access the lungs. The active substances administered in this way are generally combined with vehicles in order to achieve a reasonable dosing capacity of the medically active substance and to set further properties of the pharmaceutical powder, which for example can influence the storage life.

Proposed solutions concerning the designs of powder inhalers with which particles which can access the lungs are intended to be made available in an air stream for inhalation are described for example in EP 0 640 354 A2, U.S. Pat. No. 5,505,196, U.S. Pat. No. 5,320,714, U.S. Pat. No. 5,435,301, U.S. Pat. No. 5,301,666, DE 195 22 416 A1 and WO 97/00703. Proposals are also known to use auxiliary energy to generate the air stream, for example in ZA-A 916741.

In the drug treatment of diseases, it is generally known to use different pharmacodynamically active substances together. In medicaments in tablet form or ointment form, this has been known for a long time and is customary practice. From the pharmacological point of view, it must simply be ensured that the active substances or galenic substances do not negatively influence each other, both in terms of the effect on the body and in terms of absorption.

Also in the case of medicaments for inhalation in powder form, it is known to combine active substances by administering prepared active substance mixtures. Corresponding proposals are found in EP 0 416 951 A1 and WO 93/11773, for example for combination of salmeterol and fluticasone or formoterol and budesonide. Nevertheless, when preparing active substance mixtures in the form of loose powders, the problem remains that chemical or physical reactions of the active substances in the mixtures can cause these to change, particularly during a prolonged period of storage, which can lead to a decreased effect, inhomogeneity of the mixture, which can lead to dose variations or to undesired side effects.

To avoid such disadvantages, the pharamcodynamically active substances are therefore often administered sequentially, i.e. separately one after the other. In this connection, different administration systems are also often used for different active substances. This not only makes administration more difficult for the user, causing mix-ups, administration errors and poor compliance, but also makes such medication impractical in certain diseases. These diseases can include in particular those in which the symptoms occur in attacks and where such attacks mean that the patient's coordination and handling ability are limited by physical or psychological deficits. A typical example of this is asthma attacks.

The object of the invention is therefore to improve known systems for administration of powdered pharmaceuticals.

According to the invention, this object is achieved by a storage system for powdered pharmaceuticals, in particular for use or integration in a powder inhaler, for receiving a multiplicity of doses of at least one medically active substance, with at least two storage spaces which are separate from each other and are each intended to hold a multiplicity of doses of a medically active substance.

With the system according to the invention, it is possible to make available pharmacodynamically active substances in the form of powdered pharmaceuticals in separate storage spaces for a multiplicity of doses, yet still achieve coordinated dosing and administration of the active substances in combination, without making additional demands on the patient or medical carer, compared with a conventional inhalation of an individual pharmaceutical powder, and without additional handling requirements.

By combining separate storage spaces in the form of individual cartridges containing the same powdered pharmaceutical, the invention also makes it possible for the doctor to provide a dose very precisely adapted to the patient, without requiring a correspondingly large number of different cartridges with different metering devices.

The storage system is particularly expediently characterized in that the storage system comprises a pharmaceutical powder cartridge system for use in a medical administration device (inhaler).

For a particularly good combination of active substances, it is advantageous if the system further comprises a device for approximately simultaneous administration of pharmaceutical doses from at least two of the separate storage spaces.

In an advantageous embodiment, the pharmaceutical powder cartridge system comprises a pharmaceutical powder cartridge which has at least two storage chambers. In this case, it is expedient if the pharmaceutical powder cartridge has a metering device, and if the metering device has, for each of the storage chambers, a metering chamber for apportioning a predetermined quantity of each medically active substance provided in the storage chambers.

Particularly in the case of fixed integration in a powder inhaler, it can be advantageous if the pharmaceutical powder cartridge system has a device for bringing together the quantities of substance apportioned by the metering chambers.

For a freer combination of the active substances or dose quantities by a doctor or pharmacist, it may also be expedient, however, if the storage system comprises a pharmaceutical powder cartridge system with at least two pharmaceutical powder cartridges which each have at least one storage chamber.

In this connection, it is especially advantageous if each pharmaceutical powder cartridge has a metering device, and if each metering device has, for each of the storage chambers, a metering chamber for apportioning a predetermined quantity of each medically active substance provided in the storage chambers of the pharmaceutical powder cartridges.

Particularly if the pharmaceutical powder cartridge system with different active substance combinations is intended to be used sequentially in an inhaler, it is expedient, in order to avoid interactions of the powdered medicaments, if the pharmaceutical powder cartridge system has a device for bringing together the quantities of substance apportioned by the metering chambers.

In an advantageous embodiment, the metering devices can be coupled together.

For especially good handling, it is advantageous if the pharmaceutical powder cartridges can be coupled together mechanically.

A particularly good safeguard against incorrect medication can be obtained if, on active surfaces serving to couple the pharmaceutical powder cartridges together, the pharmaceutical powder cartridges also have indexing means which permit coupling only of pharmaceutical powder cartridges intended for this purpose. In this case, it is expedient if the indexing means have elevations and depressions which permit coupling only of pharmaceutical powder cartridges which are intended for this purpose and which have matching elevations and depressions, in particular if the elevations and depressions are arranged in the form of a matrix.

For combining cartridges for the pharmaceutical powder cartridge system according to the invention, for example by a pharmacist, it is expedient if, on their active surfaces serving to couple the pharmaceutical powder cartridges together, the pharmaceutical powder cartridges also have locking means which permit coupling of pharmaceutical powder cartridges intended for this purpose. An especially effective safeguard against manipulation by unauthorized persons or to prevent refilling of the pharmaceutical powder cartridges can be obtained if the locking means are designed in such a way that the coupled pharmaceutical powder cartridges cannot be separated from each other again without damage.

For handling by the patient, it is advantageous if the pharmaceutical powder cartridge system also has a device for indicating the quantity of pharmaceutical doses remaining in the storage chambers or removed from the storage chambers, in particular if the pharmaceutical powder cartridges can be coupled to one another and to the device for indicating the quantity of pharmaceutical doses remaining in the storage chambers or removed from the storage chambers and/or if the pharmaceutical powder cartridge system has, for each of the storage chambers, a device for indicating the quantity of pharmaceutical doses remaining in the storage chambers or removed from the storage chambers.

It is especially favourable, from the point of view of production technology, if the pharmaceutical powder cartridge system comprises two or more pharmaceutical powder cartridges which, without the locking and indexing means, are identical, show mirror-image symmetry or point-symmetry.

For a particularly versatile use, it is advantageous if the metering devices of the individual pharmaceutical powder cartridges have metering cavities of identical or different volume.

The invention can be used particularly cost-effectively in an inhaler for powdered pharmaceuticals with a pharmaceutical powder cartridge system according to one of the preceding claims as an integral part or as an exchangeable part.

APPLICATION OF THE INVENTION

With the pharmaceutical powder cartridge system according to the invention, it is possible to make available pharmacodynamically active substances in the form of powdered pharmaceuticals in separate storage spaces for a multiplicity of doses and yet still achieve coordinated dosing and administration of the active substances in combination, without making additional demands on the patient or medical carer, compared with a conventional inhalation of an individual pharmaceutical powder, and without additional handling requirements.

It is also possible to make available powdered pharmaceuticals, in active substance combinations for individual inhalation, whose individual active substances are incompatible with each other as regards storage life, their stability or their dosability.

Without implying any limitation, possible examples of such active substance combinations are: budesonide combined with formoterol, fluticasone combined with formoterol, fluticasone combined with salmeterol, fenoterol combined with ipatropium bromide, glycopyrrolate combined with formoterol, loteprednol combined with formoterol, loteprednol combined with glycopyrrolate, mometasone with formoterol, mometasone combined with salmeterol, disodium cromoglycate with reproterol.

Elements for active substance combinations, for which the invention can be applied, can also include, for example, from the group of beta-sympathomimetics: salbutamol, reproterol, fenoterol, formoterol, salmeterol. Possible examples from the group of corticosteroids are: budesonide, beclomethasone, fluticasone, triamcinolone, loteprednol, mometasone, flunisolide, ciclosonide. Possible examples from the group of anticholinergics are: ipatropium bromide, thiotropium bromide, glycopyrrolate.

Possible examples from the group of analgesics and antimigraines are: morphine, tramadol, flupirtine, sumatryptan. The following can be used from the group of peptides and proteins: cetrorelix, insulin, calcitonin, parathyroid hormone, factor VIII analogs, interferon alpha, interferon beta, heparin, FSH (follicle-stimulating hormone), colistin, tobramycin.

Use is not limited to the active substances mentioned here. The pharmaceutical powder cartridge system described is suitable for all active substances which can be metered in powder form and administered by inhalation. By appropriate modification of the system and of the metering device, the invention described is also suitable for combination of active substances which contain liquid formulations, for example solutions or suspensions of pharmacodynamically active substances.

Pharmaceutical powder formulations which can expediently be used with the pharmaceutical powder cartridge system according to the invention can contain various active substances, such as, for example, analgesics, anti-allergics, antibiotics, anticholinergics, antihistamines, anti-inflammatory substances, antipyretics, corticoids, steroids, antitussives, bronchodilators, diuretics, enzymes, cardiovascular agents, hormones, proteins and peptides. Examples of analgesics are codeine, diamorphine, dihydromorphine, ergotamine, fentanyl and morphine; examples of anti-allergics are cromoglycinic acid and nedocromil; examples of antibiotics are cephalosporins, fusafungine, neomycin, penicillins, pentamidine, streptomycin, sulphonamides and tetracyclines, colistin, tobramycin; examples of anticholinergics are atropine, atropine methonitrate, ipratropium bromide, oxitropium bromide, trospium chloride and thiotropium bromide; examples of antihistamines are azelastine, flezelastine and methapyrilene; examples of anti-inflammatory substances are beclomethasone, budesonide, loteprednol, dexamethasone, flunisolide, fluticasone, tipredane, triamcinolone, mometasone; examples of antitussives are narcotine and noscapine; examples of bronchodilators are bambuterol, bitolterol, carbuterol, clenbuterol, ephedrine, epinephrine, formoterol, fenoterol, hexoprenaline, ibuterol, isoprenaline, isoprotenerol, metaproterenol, orciprenaline, phenylephrine, phenylpropanolamine, pirbuterol, procaterol, reproterol, rimiterol, salbutamol, salmeterol, sulfonterol, terbutaline and tolobuterol; examples of diuretics are amiloride and furosemide; an example of an enzyme is trypsin; examples of cardiovascular agents are diltiazem and nitroglycerin; examples of hormones are cortisone, hydrocortisone and prednisolone; examples of proteins and peptides are cyclosporine, cetrorelix, glucagon and insulin. Further active substances which can be used are adrenochrome, colchicine, heparin, scopolamine. The active substances listed by way of example can be used as free bases or acids or as pharmaceutically acceptable salts. Counterions which can be used include, for example, physiological alkaline earth metals or alkali metals or amines, for example acetate, benzene sulphonate, benzoate, hydrogen carbonate, hydrogen tartrate, bromide, chloride, iodide, carbonate, citrate, fumarate, malate, maleate, cluconate, lactate, pamoate and sulphate. Esters can also be used, for example acetate, acetonide, propionate, diproprionate, valerate.

However, the invention not only permits the combined administration of different powdered pharmaceuticals in equal or different individual doses, but also, by combining individual cartridges with the same powdered pharmaceutical, makes it possible for the doctor to provide a dose very precisely adapted to the patient, without requiring a correspondingly large number of different cartridges with different metering devices, by comparison with, for example, the cartridge known from WO 97/00703.

If the individual cartridges are arranged, for example, in a series of dose volumes of 1, 3 and 5 ml, dose volumes of 1, 2, 3, 4, 5, 6, 8, 10 ml can be obtained using just one individual cartridge or by replacing the second cartridge by a dummy as a safeguard.

The invention will be explained in greater detail below with reference to illustrative embodiments.

FIG. 2 shows a longitudinal section through a pharmaceutical powder cartridge system according to the invention;

FIG. 3 shows a cross section through the pharmaceutical powder cartridge system according to the invention, along the line A-A in FIG. 2;

FIG. 4 shows a longitudinal section through a pharmaceutical cartridge of the pharmaceutical powder cartridge system according to the invention, along the line B-B in FIG. 3;

FIG. 5 shows a longitudinal section through a pharmaceutical cartridge of the pharmaceutical powder cartridge system according to the invention, as in FIG. 2 (secondary cartridge);

FIG. 6 shows a longitudinal section through another pharmaceutical cartridge of the pharmaceutical powder cartridge system according to the invention, as in FIG. 2 (primary cartridge);

FIG. 7 shows a view of a pharmaceutical cartridge of the pharmaceutical powder cartridge system according to the invention (reverse of the illustration in FIG. 2) (primary cartridge);

FIG. 8 shows a view of a pharmaceutical cartridge of the pharmaceutical powder cartridge system according to the invention, similar to FIG. 2 (secondary cartridge); and FIG. 9 shows a side view of the pharmaceutical cartridge of the pharmaceutical powder cartridge system according to the invention (primary cartridge).

Figure 1:
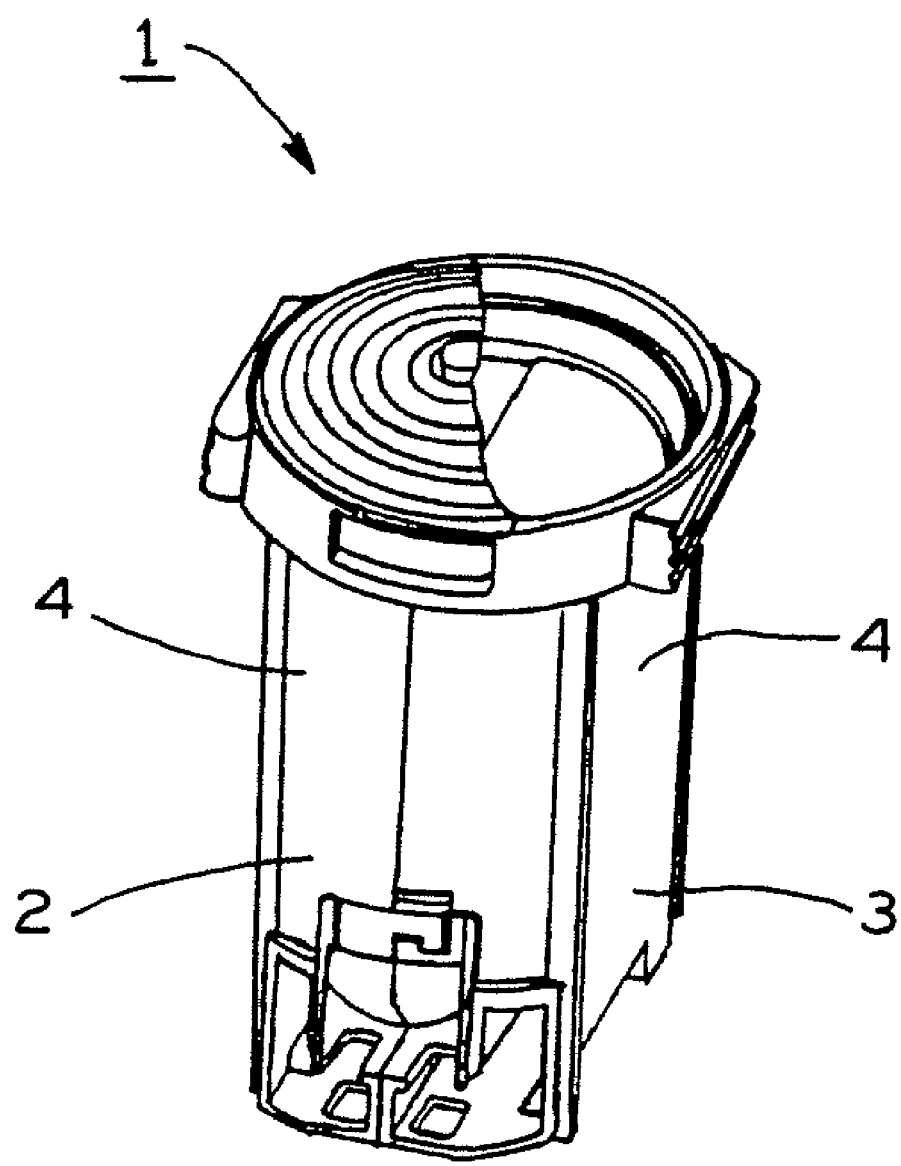
FIG. 1 shows a pharmaceutical powder cartridge system according to the invention, in a perspective view.

FIG. 1 shows a perspective view of a storage system according to the invention, here in the form of a pharmaceutical powder cartridge system 1 which can be fitted in an exchangeable manner into a powder inhaler. The pharmaceutical powder cartridge system 1 shown here consists of two pharmaceutical powder cartridges 2 and 3, each with a storage chamber 4 for a pharmaceutical powder.

A longitudinal section through the pharmaceutical powder cartridge system 1 is shown in FIG. 2. Here too, it is clearly evident that the pharmaceutical powder cartridge system 1 in this case consists of two individual cartridges 2 and 3. For the sake of clarity, a distinction is made hereinafter between the primary cartridge 2 and the secondary cartridge 3. Each of the pharmaceutical powder cartridges 2 and 3 comprises a storage chamber 4 for receiving the same pharmaceutical powder or different pharmaceutical powders, as has already been explained.

Moreover, each of the pharmaceutical powder cartridges 2 and 3 has a metering device in the form of a metering slide 5. Each of the metering slides 5 comprises a metering cavity 6, whose receiving volume forms the dose quantity which is to be made available for an inhalation.

As can be seen from FIG. 3, a cross section through the pharmaceutical powder cartridge system 1 along the line A-A in FIG. 2 at the level of the metering slides 5, the metering slides 5 are displaceable in a metering slide channel 7, at least from the filling position shown to an emptying position. For the sake of simplicity, the metering slides 5 of the primary cartridge 2 and of the secondary cartridge 3 are here shown as being mirror images of each other and with metering cavities 6 of the same size.

In the filling position represented in FIG. 3, it is possible, as can be clearly seen from FIG. 2, for pharmaceutical powder to fall from the storage chambers 4 into the metering cavities 6. When the metering cavities 6 are filled with a pharmaceutical powder as desired, the metering slides 5 can be moved into an emptying position (not shown) by engagement means (not shown) of a powder inhaler, for example as described in U.S. Pat. No. 5,840,279. The engagement means of the powder inhaler in this case expediently project through recesses 8 provided correspondingly in the lower areas of the primary cartridge 2 and of the secondary cartridge 3.

The emptying position is reached when the metering cavities 6 are located over the dispensing openings 9. When the metering slides 5 have reached this position, the pharmaceutical powder can fall from the metering cavities 6 through the dispensing openings 9, for example into a powder channel (not shown) of an inhaler.

If different pharmaceutical powders are accommodated in the storage chambers 4 of the primary cartridge 2 and of the secondary cartridge 3, the pharmaceutical powders then mix together in the powder channel of the inhaler, as far as possible assisted by the inhalation air stream.

FIG. 4 shows a longitudinal section through the secondary cartridge 3 along the line B-B in FIG. 2. The filling position of the metering slide 5 can be clearly seen here, with the metering cavity 6 underneath the hole 10 on the underside of the storage chamber 4. To reach the emptying position, the metering slide 5 in FIG. 4 is moved to the right until this metering cavity 6 is flush with the dispensing opening 9 and the pharmaceutical powder can fall downwards.

After the secondary cartridge 3 has been filled with a pharmaceutical, the top of the storage chamber 4 of the secondary cartridge 3 is closed off, for example, by means of a stable foil cover 11, e.g. by ultrasonic welding or in some other suitable manner.

In FIG. 5, the secondary cartridge 3 is shown in the same way as in FIG. 2, but without the metering slide 5 and the primary cartridge 2.

The primary cartridge 2 is shown accordingly in FIG. 6. As can be seen from FIG. 2, a metering slide is arranged on the underside of the primary cartridge 2, in the same way as for the secondary cartridge 3. The mode of action and the operation of the metering slide correspond to those of the metering slide of the secondary cartridge 3, as has been described above.

By contrast, the primary cartridge 2 has an upper area 12 which, when the two cartridges 2 and 3 are joined together, also covers the secondary cartridge 3, as can be seen clearly from FIG. 2.

In the illustrative embodiment shown, a device for indicating the quantity of pharmaceutical doses remaining in the storage chambers 4 or removed from the storage chambers 4 is provided in the upper area 12 in an annular channel 13 (but not shown in detail).

This indicator can be formed, for example, by film strips with corresponding markings, as is described in detail in WO 97/00703. Accordingly, the storage chamber 4 is closed off in the upper area 12 of the primary cartridge 2 by a lid 14 which at the same time also covers the annular channel 13 for the film strip for indicating the pharmaceutical doses. The top of the lid 14 is in this case designed as an undulated spring 15 in order not only to close off the storage space elastically, but also to ensure via the central pin 16 a length equalization and a substantially clearance-free fit of the pharmaceutical powder cartridge system 1 in a suitable inhaler. Such an inhaler is described in outline also in WO 97/00703.

Also provided in the upper area 12 of the primary cartridge 2, connected to the annular channel 13, there is a recess 17 for engagement of a drive means of an inhaler for driving the indicator element for the number of pharmaceutical doses remaining or removed.

It is also expedient to provide a viewing window 18 in the upper area 12, at the level of the annular channel 13 in the primary cartridge 12, which viewing window 18 makes it possible to read off the device for indicating doses of pharmaceutical removed or remaining (FIG. 7). FIG. 7 also clearly shows that the primary cartridge 2 is provided with hook elements 19 which can cooperate with corresponding depressions 20 in the secondary cartridge 3 (FIG. 8). Also provided in the wall 21 of the secondary cartridge 3 facing towards the primary cartridge 2 is a wedge-shaped projection 22 which, when the secondary cartridge 3 is pushed from below into a recess 23 in the upper area 12 of the primary cartridge 2, leads to elastic deformation of the wall 21 and engages with a correspondingly designed depression 24 in the wall 25 of the primary cartridge 2 facing towards the secondary cartridge 3 as soon as the secondary cartridge 2 has reached its intended seat. The depression 24 and the interaction with the hook elements 19 of the primary cartridge 2 ensure that the secondary cartridge 3 cannot move laterally away from the primary cartridge 2 after assembly. The engagement of the wedge-shaped projection 22 with the associated depression 24 in the primary cartridge 2 ensures that the secondary cartridge can no longer be pulled down in order to disconnect the hook elements 19 and the depression 24 (FIG. 9). After such assembly, the primary cartridge 2 and the secondary cartridge 3 can only be separated from each other again by destroying them.

A suitable indexing can also be provided on the walls 25 and 21 facing each other. This can be effected, for example, in the form of indexed depressions and projections in the manner of a key. In another arrangement for preventing separation of the cartridge after assembly, a correspondingly indexed matrix with pin-like projections and holes can also be used.

It will of course be appreciated that other embodiments of the pharmaceutical powder cartridge system according to the invention are also conceivable, for example two symmetric or asymmetric cartridges which have separate indicators for the doses removed or still remaining, or symmetric or asymmetric cartridges which are mounted together with a head element which contains a corresponding indicator.

REFERENCE NUMBERS

1 Pharmaceutical powder cartridge system
2 Primary cartridge
3 Secondary cartridge
4 Storage chamber
5 Metering slide
6 Metering cavity
7 Metering slide channel
8 Recess
9 Dispensing opening
10 Hole
11 Foil cover
12 Upper area of 2
13 Annular channel
14 Lid
15 Undulated spring
16 Pin
17 Recess in 13

18 Viewing window
19 Hook element
20 Depression
21 Wall
22 Wedge-shaped projection
23 Recess of 12
24 Depression
25 Wall

The invention claimed is:

1. A cartridge insertable within a powder inhaler for storing and enabling substantially simultaneous administration of several powdered pharmaceuticals, comprising:
an unpressurized first storage compartment including a first closure member, and a first metering cavity and associated first metering slide;
an unpressurized second storage compartment separate from said first storage compartment, said first and second storage compartments removably coupled to one another, said second storage compartment including a second closure member separate from said first closure member, and a second metering cavity and associated second metering slide;
said first and second metering slides operable to simultaneously apportion a predetermined quantity of a powdered, medically active substance from each said first and second storage compartments.

2. The cartridge of claim 1, wherein said first and second storage compartments each have an indexing device which only permits coupling together of preselected said first and second storage compartments.

3. The cartridge of claim 2, wherein said indexing device comprises at least one protrusion on one of said first and second storage compartments and at least one depression located on the other of said first and second storage compartments, each said protrusion matable with a said depression.

4. The cartridge of claim 3, wherein said protrusions and depressions are arranged in the form of a matrix.

5. The cartridge of claim 1, further comprising a locking device lockingly coupling together said first and second storage compartments.

6. The cartridge of claim 5, wherein said locking device permanently couples said first and second storage compartments together whereby said first and second storage compartments cannot be separated without damaging said first and second storage compartments.

7. A cartridge insertable within a powder inhaler for storing and enabling substantially simultaneous administration of several powdered pharmaceuticals, comprising:
an unpressurized first storage compartment including a first closure member, and a first metering cavity and associated first metering slide;
an unpressurized second storage compartment separate from said first storage compartment, said second storage compartment including a second closure member separate from said first closure member, and a second metering cavity and associated second metering slide;
said first and second metering slides operable to simultaneously apportion a predetermined quantity of a powdered, medically active substance from each said first and second storage compartments; and
said first storage compartment including a wall that overlaps and covers said second closure member of said second storage compartment.

8. A cartridge insertable within a powder inhaler for storing and enabling substantially simultaneous administration of several powdered pharmaceuticals, comprising:
an unpressurized first storage compartment including a first closure member, and a first metering cavity and associated first metering slide;
an unpressurized second storage compartment separate from said first storage compartment, said second storage compartment including a second closure member separate from said first closure member, and a second metering cavity and associated second metering slide;
said first and second metering slides operable to simultaneously apportion a predetermined quantity of a powdered, medically active substance from each said first and second storage compartments; and
said first closure member of said first storage compartment overlapping said second closure member of said second storage compartment.

9. A cartridge insertable within a powder inhaler for storing and enabling substantially simultaneous administration of several powdered pharmaceuticals, comprising:
an unpressurized first storage compartment including a first closure member, and a first metering cavity and associated first metering slide;
an unpressurized second storage compartment separate from said first storage compartment, said second storage compartment including a second closure member separate from said first closure member, and a second metering cavity and associated second metering slide;
said first and second metering slides operable to simultaneously apportion a predetermined quantity of a powdered, medically active substance from each said first and second storage compartments; and
said closure member of said first storage compartment including an undulated spring.

10. A cartridge insertable within a powder inhaler for storing and enabling substantially simultaneous administration of several powdered pharmaceuticals, comprising:
an unpressurized first storage compartment including a first closure member, and a first metering cavity and associated first metering slide;
an unpressurized second storage compartment separate from said first storage compartment, said second storage compartment including a second closure member separate from said first closure member, and a second metering cavity and associated second metering slide;
said first and second metering slides operable to simultaneously apportion a predetermined quantity of a powdered, medically active substance from each said first and second storage compartments; and
an indicator for indicating at least one of a quantity of pharmaceutical doses remaining in at least one of said first and second storage compartments, said indicator is received within an annular channel in said first storage compartment, said closure member of said first storage compartment covering said annular channel.

* * * * *